(12) United States Patent
Gliner

(10) Patent No.: US 11,523,942 B2
(45) Date of Patent: Dec. 13, 2022

(54) MEDICAL SUCTION TOOL FOR A EUSTACHIAN TUBE

(71) Applicant: Biosense Webster (Israel) Ltd., Yokneam (IL)

(72) Inventor: Vadim Gliner, Haifa (IL)

(73) Assignee: Biosense Webster (Israel) Ltd., Yokneam (IL)

(*) Notice: Subject to any disclaimer, the term of this patent is extended or adjusted under 35 U.S.C. 154(b) by 524 days.

(21) Appl. No.: 15/674,369

(22) Filed: Aug. 10, 2017

(65) Prior Publication Data
US 2019/0046358 A1 Feb. 14, 2019

(51) Int. Cl.
| | | |
|---|---|---|
| A61M 31/00 | (2006.01) | |
| A61M 25/00 | (2006.01) | |
| A61M 1/00 | (2006.01) | |
| A61F 11/20 | (2022.01) | |
| A61B 34/20 | (2016.01) | |

(Continued)

(52) U.S. Cl.
CPC ............ *A61F 11/202* (2022.01); *A61B 34/20* (2016.02); *A61F 11/20* (2022.01); *A61M 1/0023* (2013.01); *A61M 25/005* (2013.01); *A61M 25/0012* (2013.01); *A61M 25/0127* (2013.01); *A61B 2034/2051* (2016.02); *A61M 2025/0004* (2013.01); *A61M 2025/0039* (2013.01);
(Continued)

(58) Field of Classification Search
CPC ...... A61F 11/002; A61F 11/004; A61B 34/20; A61B 2034/2051; A61M 25/0012; A61M 25/005; A61M 25/0127; A61M 1/0023; A61M 2025/0004; A61M 2025/0039; A61M 2205/0266; A61M 2207/00; A61M 2210/0675; A61M 1/0025; A61M 1/0066; A61M 1/008; A61M 2210/0618; A61M 2210/005
See application file for complete search history.

(56) References Cited

U.S. PATENT DOCUMENTS

| | | |
|---|---|---|
| 5,391,199 A | 2/1995 | Ben-Haim |
| 5,462,529 A | 10/1995 | Simpson et al. |

(Continued)

FOREIGN PATENT DOCUMENTS

| | | |
|---|---|---|
| CN | 101861184 A | 10/2010 |
| CN | 102488955 A | 6/2012 |

(Continued)

OTHER PUBLICATIONS

European Search Report dated Oct. 12, 2018 from corresponding European Patent Application No. 18188211.9.
(Continued)

*Primary Examiner* — Tatyana Zalukaeva
*Assistant Examiner* — Ilya Y Treyger
(74) *Attorney, Agent, or Firm* — Frost Brown Todd LLC

(57) ABSTRACT

A method includes inserting into a patient body a medical suction tool, which includes a hollow first tube for removing material away from a Eustachian tube of a patient, and a hollow second tube disposed around the first tube. The medical suction tool is navigated to the Eustachian tube. The Eustachian tube is sealed by coupling an outer surface of the second tube to an inner surface of the Eustachian tube. While the Eustachian tube is sealed by the second tube, the material is removed away from the Eustachian tube via the first tube.

18 Claims, 3 Drawing Sheets

(51) Int. Cl.
*A61M 25/01* (2006.01)
*A61M 27/00* (2006.01)

(52) U.S. Cl.
CPC . *A61M 2205/0266* (2013.01); *A61M 2207/00* (2013.01); *A61M 2210/0675* (2013.01)

(56) References Cited

U.S. PATENT DOCUMENTS

| | | | |
|---|---|---|---|
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0240147 A1* | 10/2005 | Makower | A61B 17/24 604/96.01 |
| 2007/0233036 A1* | 10/2007 | Mandpe | A61F 11/002 604/514 |
| 2008/0287908 A1 | 11/2008 | Muni et al. | |
| 2011/0144571 A1* | 6/2011 | Ahluwalia | A61M 1/0064 604/30 |
| 2013/0303968 A1 | 11/2013 | Chifford et al. | |
| 2014/0200444 A1* | 7/2014 | Kim | A61M 25/09041 600/424 |
| 2014/0276654 A1* | 9/2014 | Jenkins | A61M 1/008 604/540 |
| 2014/0296898 A1* | 10/2014 | Chang | A61B 17/24 606/170 |
| 2015/0202089 A1 | 7/2015 | Campbell et al. | |
| 2016/0310042 A1* | 10/2016 | Kesten | A61B 5/055 |
| 2017/0119473 A1* | 5/2017 | Clopp | A61B 34/20 |
| 2017/0119993 A1* | 5/2017 | Desai | A61M 25/0068 |
| 2017/0143938 A1* | 5/2017 | Ogle | A61B 17/22 |

FOREIGN PATENT DOCUMENTS

| | | |
|---|---|---|
| CN | 105263556 A | 1/2016 |
| EP | 2535079 | 12/2012 |
| JP | 2003-299634 A | 10/2003 |
| JP | 2008-539973 A | 11/2008 |
| JP | 2013-515591 A | 5/2013 |
| WO | WO 9605768 | 2/1996 |

OTHER PUBLICATIONS

Chinese Office Action and Search Report dated May 30, 2022, for Application No. 201810906664.2, 13 pages.

Japanese Notification of Reasons for Refusal dated Aug. 23, 2022, for Application No. 2018-150088, 4 pages.

* cited by examiner

MEDICAL SUCTION TOOL FOR A EUSTACHIAN TUBE

FIELD OF THE INVENTION

The present invention relates generally to medical devices, and particularly to methods and systems for suctioning material from a Eustachian tube of a patient.

BACKGROUND OF THE INVENTION

Some ear-nose-throat (ENT) procedures require removing material, such as liquid or mucus, from the Eustachian tube and sinuses of a patient.

For example, U.S. Patent Application Publication 2013/0303968, issued as U.S. Pat. No. 9,072,626 on Jul. 7, 2015, describes methods and devices for providing a gas pathway between the nasopharynx and the Eustachian tube. One device may include a lumen with a valve. A portion of the valve may be tethered to adjacent muscle. Another portion of the valve may be tethered to adjacent cartilage.

U.S. Patent Application Publication 2014/0296898, now abandoned, describes various methods and devices used for remodeling or changing the shape, size or configuration of a sinus ostium or duct or other anatomical structure in the ear, nose or throat, removing matter from the ear, nose or throat, delivering diagnostic or therapeutic substances or performing other diagnostic or therapeutic procedures.

SUMMARY OF THE INVENTION

An embodiment of the present invention that is described herein provides a method that includes inserting into a patient body a medical suction tool, which includes a hollow first tube for removing material away from a Eustachian tube of a patient, and a hollow second tube disposed around the first tube. The medical suction tool is navigated to the Eustachian tube. The Eustachian tube is sealed by coupling an outer surface of the second tube to an inner surface of the Eustachian tube. While the Eustachian tube is sealed by the second tube, the material is removed away from the Eustachian tube via the first tube.

In some embodiments, at least one of the first and second tubes is flexible. In other embodiments, navigating the medical suction tool includes tracking a position of the medical suction tool using a position sensor of a position tracking system, which is coupled to a distal end of the medical suction tool and produces position signals that are indicative of the position of the position sensor. In yet other embodiments, tracking the position includes tracking a magnetic position sensor that includes a single coil.

In an embodiment, inserting the medical suction tool includes inserting the medical suction tool through a nose of the patient. In another embodiment, the method includes cleaning the Eustachian tube by moving the medical suction tool along sidewalls of the Eustachian tube. In yet another embodiment, removing the material includes drawing the material away from the Eustachian tube by applying suction using a suction apparatus coupled to the medical suction tool.

There is additionally provided, in accordance with an embodiment of the present invention, a medical suction tool that includes a hollow first tube and a hollow second tube. The hollow first tube is coupled to a suction apparatus and is configured to remove material away from a Eustachian tube of a patient. The hollow second tube is disposed around the first tube, and configured to seal the Eustachian tube by coupling an outer surface of the second tube to an inner surface of the Eustachian tube.

There is further provided, in accordance with an embodiment of the present invention, a method for producing a medical suction tool, the method includes coupling to a suction apparatus a hollow first tube for removing material away from a Eustachian tube of a patient. A hollow second tube is disposed around the first tube for sealing the Eustachian tube by coupling an outer surface of the second tube to an inner surface of the Eustachian tube.

The present invention will be more fully understood from the following detailed description of the embodiments thereof, taken together with the drawings in which:

DETAILED DESCRIPTION OF EMBODIMENTS

Overview

Figure 1:
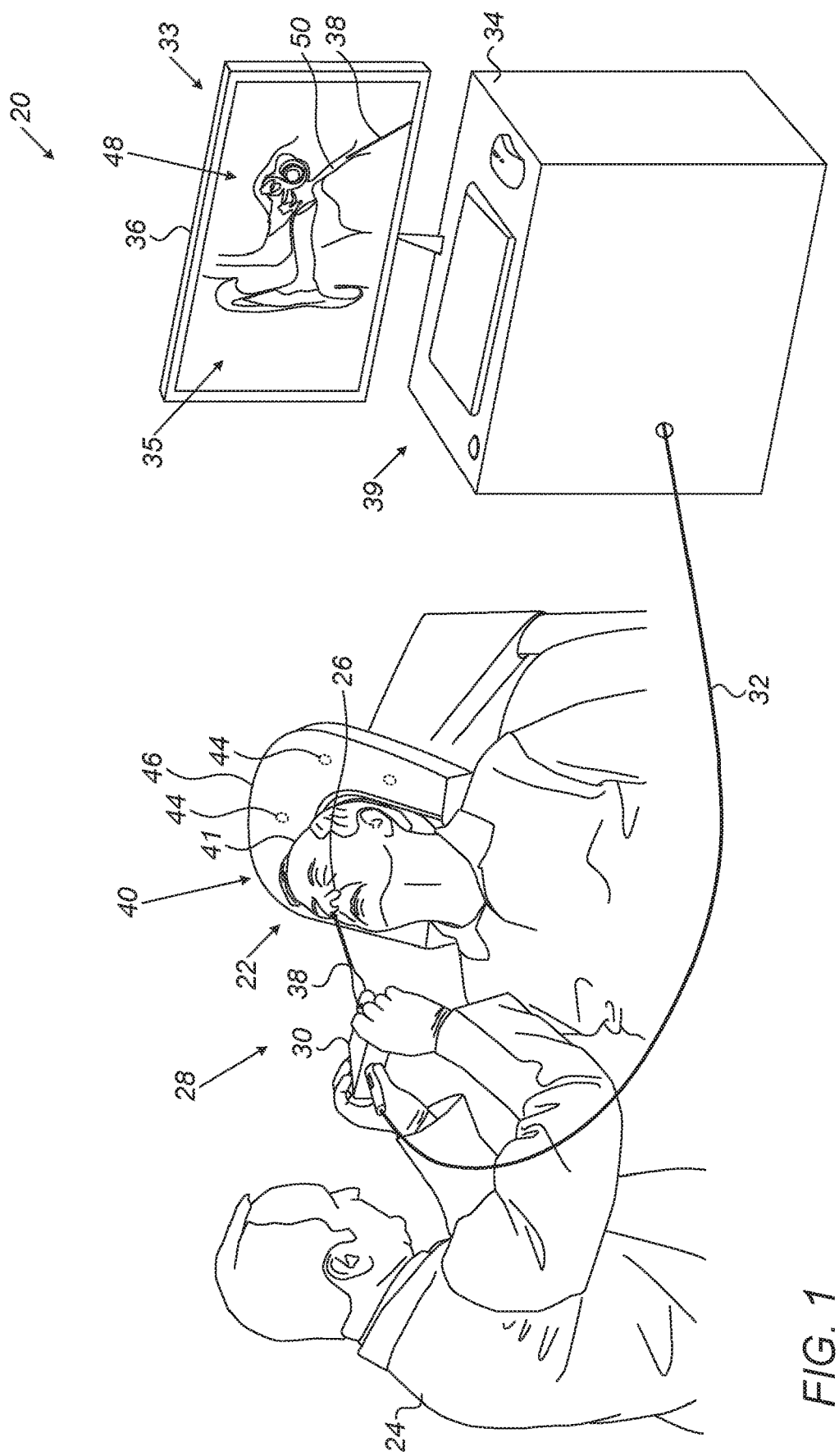
FIG. 1 is a schematic, pictorial illustration of a sinuplasty procedure using a sinuplasty system, in accordance with an embodiment of the present invention.

Some medical procedures, such as sinuplasty, require removing material from anatomical cavities, such as a Eustachian tube of a patient inner ear. The Eustachian tube is typically narrow and cannot be accessed through the outer ear without damaging the ear drum and organs of the inner ear. In principle, it is possible to insert a suction device into a cavity (e.g., sinus) located some distance away from the Eustachian tube, but the suction will be ineffective due to lack of sealing between the suction device and the Eustachian tube.

Embodiments of the present invention that are described hereinbelow provide improved techniques for suctioning undesired material, such as mucus and infectious fluid, from the Eustachian tube. In some embodiments, a suction module for suctioning the undesired material comprises a suction tool coupled to a suction apparatus, such as a medical suction pump.

In some embodiments, the suction tool comprises a hollow flexible internal tube, which is coupled, at its proximal end, to the suction pump, and configured to remove the undesired material away from the Eustachian tube. The suction tool further comprises a hollow flexible external tube, which is disposed around the internal tube. The external tube is configured to seal the Eustachian tube by coupling its outer surface to an inner surface of the Eustachian tube.

In some embodiments, a position sensor of a position tracking system is coupled to the distal tip of the suction tube and configured to produce position signals that are indicative of a position of the suction tool in an organ, such as an ear-nose-throat (ENT) system, of the patient.

In some embodiments, the suction module is electrically connected to a processor, which is configured to receive pre-acquired anatomical images, such as computerized tomography (CT) images depicting respective segmented two-dimensional (2D) slices of the patient ENT, from a CT system, and to register between coordinate systems of the CT system and the position tracking system.

In some embodiments, the processor is further configured to track the position of the distal tip in the patient body, and to display a marker on a respective anatomical image, indicative of the position of the position sensor in the anatomical image.

In some embodiments, during the sinuplasty procedure, the physician inserts the suction tool, through the patient nose, and navigates the suction tool to an ostium of the Eustachian tube, using the marker displayed on the anatomical image.

In some embodiments, the physician seals the Eustachian tube by coupling the outer surface of the external tube to the inner surface of the Eustachian tube.

Subsequently, the physician removes the undesired material from the Eustachian tube by applying suction using the suction pump coupled to the proximal end of the suction tool. After concluding the material removal, the physician extracts the suction tool, through the patient nose, out of the body of the patient.

System Description

FIG. 1 is a schematic pictorial illustration of a sinuplasty procedure using a sinuplasty system 20, in accordance with an embodiment of the present invention. In some embodiments, sinuplasty system 20 comprises an ear-nose-throat (ENT) suction module 28, which is configured to remove matter, such as infection, liquid or mucus, from a Eustachian tube 50 of a patient 22.

In some embodiments, suction module 28 comprises a distal end, such as an ENT suction tool 38, which a physician 24 inserts into a nose 26 of patient 22. Module 28 further comprises a handheld suction apparatus 30, coupled to a proximal end of suction tool 38 and configured to assist physician 24 in navigating tool 38 into Eustachian tube 50 and in applying suction, so as to remove the matter away from Eustachian tube 50. ENT suction tool is depicted in further detail in FIG. 2 below.

In an embodiment, system 20 further comprises a magnetic position tracking system, which is configured to track the position of one or more position sensors in the head of patient 22. The magnetic position tracking system comprises magnetic field-generators 44 and one or more position sensors shown in FIG. 2 below. The position sensors generate position signals in response to the sensed external magnetic fields from the field generators, thereby enabling a processor 34 to map the position of each sensor as will be described below.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004; 2003/0120150 A1, issued as U.S. Pat. No. 7,729,742 on Jun. 1, 2010; and 2004/0068178 A1, now abandoned, whose disclosures are all incorporated herein by reference.

System 20 further comprises a location pad 40, which comprises field-generators 44 fixed on a frame 46. In the exemplary configuration shown in FIG. 1, pad 40 comprises five field-generators 44 but may comprise any other suitable number of generators 44. Pad 40 further comprises a pillow (not shown) placed under a head 41 of patient 22, such that generators 44 are located at fixed, known positions external to patient 22.

In some embodiments, system 20 comprises a console 33, which comprises a processor 34, typically a general-purpose computer, with suitable front end and interface circuits for receiving signals from tool 28 having a magnetic sensor attached thereon (shown in FIG. 2 below), via a cable 32, and for controlling other components of system 20 described herein.

In some embodiments, processor 34 is configured to map the position of each position sensor so as to estimate the position and orientation of a distal tip (shown in FIG. 2 below) of tool 28 in the coordinate system of the optical position tracking system.

In some embodiments, processor 34 is configured to receive one or more anatomical images, such as computerized tomography (CT) images depicting respective segmented two-dimensional (2D) slices of a head 41 of a patient 22, obtained using an external CT system (not shown). The term "segmented" refers to displaying various types of tissues identified in each slice by measuring respective attenuation of the tissues in the CT system.

Console 33 further comprises input devices 39 and a user display 36, which is configured to display the data (e.g., images) received from processor 34 or inputs inserted by a user (e.g., physician 24).

In some embodiments, processor 34 is configured to display from among the CT images, one or more selected slices, such as an image 35, on user display 36. In the example of FIG. 1, image 35 is a sectional view of an ear 48 of patient 22, such that image 35 comprises Eustachian tube 50.

Console 33 comprises a driver circuit (not shown), which is configured to drive field-generators 44 with suitable signals so as to generate magnetic fields in a predefined working volume around head 41.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and from the corresponding description.

Processor 34 may be programmed in software to carry out the functions that are used by the system, and to store data in a memory (not shown) to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Figure 2:
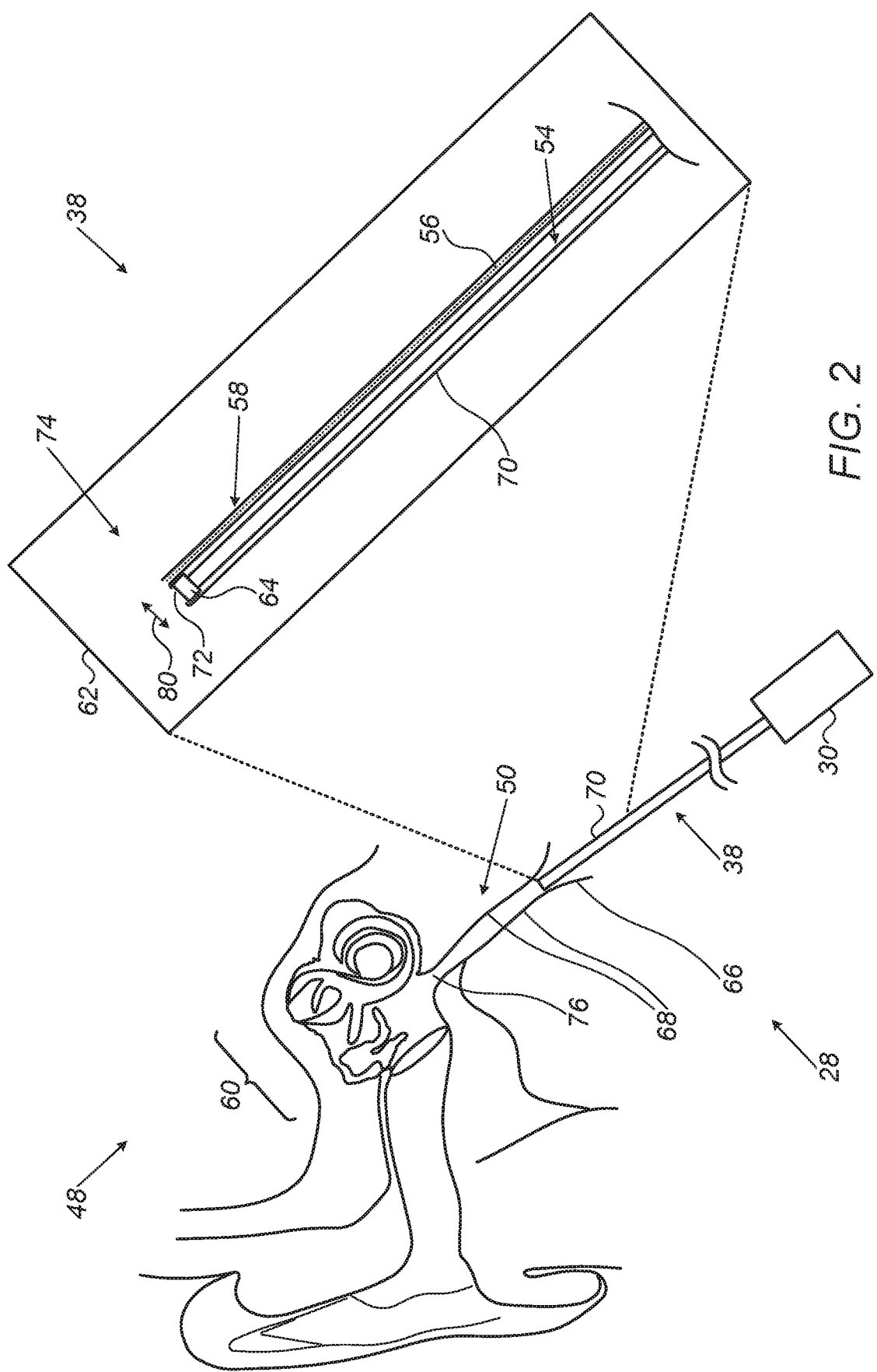
FIG. 2 is a sectional side view of an ear and a suction module, in accordance with an embodiment of the present invention.

FIG. 2 is a sectional side view of ear 48 and suction module 28, in accordance with an embodiment of the present invention. During the sinuplasty procedure, physician 24 inserts suction tool 38, typically through nose 26, into an ostium 66 of Eustachian tube 50. Note that suction tool 38 is coupled to suction apparatus 30, located externally to patient 22 and may be used by physician 24 for navigating suction tool 38 from nose 26 to Eustachian tube 50 of ear 48. Additionally or alternatively, any other suitable apparatus may be used by physician for the navigation of suction tool 38.

Reference is now made to an inset 62 showing the distal end of suction tool 38. In some embodiments, suction tool 38 comprises an internal hollow tube 54, which is typically flexible but can also be rigid, and an external hollow tube 58 disposed around internal hollow tube 54. External hollow tube 58 is typically flexible but may also be rigid.

In some embodiments, tubes 54 and 58 are typically made from polymers, such as polyurethane and polyamide, or from any other suitable biocompatible material. In an embodiment, suction tube 38 is produced such that an outer diameter 80 of the distal end of tube 38 has a similar value to an inner diameter (i.e., between inner surfaces 68) of Eustachian tube 50, e.g., about 1 mm. Note that the inner diameter of Eustachian tube 50 may be measured, e.g., in image 35, before performing the sinuplasty procedure, so that physician 24 may select a suction tool having a suitable external diameter that can fit into Eustachian tube 50. In this embodiment, when physician inserts suction tool 38 into ostium 66, suction tool 38 is configured to seal Eustachian tube 50 by coupling an outer surface 70 of external tube 58 to inner surface 68 of Eustachian tube 50.

Reference is now made back to inset 62. In some embodiments, openings in a distal tip 74 of hollow tubes 54 and 58 form an opening 72, through which suction tool 38 removes material away (e.g., liquid, mucus, infection, dirt) from cavities in an inner ear 60, and/or from Eustachian tube 50.

In some embodiments, suction tool 38 comprises a strengthening element, such as a wire 56 that extends along at least part (e.g., the distal end) of external tube 58 and is coupled thereto. In an embodiment, wire 56 is made from an alloy of nickel-titanium, such as nitinol, or any other suitable material, and is configured to mechanically strengthen external tube 58.

In some embodiments, suction tool 38 further comprises a position sensor 64 of the position tracking system described in FIG. 1 above. In some embodiments, position sensor 64 comprises a single coil configured to generate position signals, or any other suitable number of coils. In the example of FIG. 2 position sensor 64 is coupled to distal tip 74 of suction tool 38, such that sensor 64 does not block opening 72. In this configuration, sensor 64 may be coupled between an outer surface of tube 54 and an inner surface of tube 58, such that electrical leads (not shown) connected to sensor 64 are disposed between these surfaces and configured to conduct the position signal sensed by position sensor 64 to cable 32.

In other embodiments, sensor 64 may be coupled to surface 70 of tube 58, or in any other suitable configuration in distal tip 74.

In alternative embodiments, sensor 64 may be coupled along suction tool 38 at any suitable offset relative to distal tip 74, such that processor 34 applies the offset to calculate the position of distal tip 74 in the coordinate system of the position tracking system.

In some embodiments, processor 34 is configured to register between coordinate systems of the CT system and the position tracking system. In an embodiment, processor 34 is configured to display, based on the registered coordinate systems, an indication of the position of distal tip 74 in image 35, so as to assist physician 24 in navigating distal tip 74 into ostium 66.

In some embodiments, suction tool 38 is further configured to clean Eustachian tube 50 from any undesired material (e.g., dirt, mucus, infectious fluid), for example, by peeling and suctioning the dirt from surface 68. The cleaning may be carried out by an operator, such as physician 24, which moves suction tool 38, e.g., back and forth between ostium 66 and an ostium 76, along surface 68 of Eustachian tube 50. In some embodiments, physician 24 can see the position of distal tip 74 in image 35, so as to pull suction tool 38 back before reaching ostium 76.

The configurations of suction module 28, and particularly, suction tool 38 described in FIGS. 1 and 2 above, are depicted purely by way of example. In alternative embodiments, module 28 and tool 38 may comprise any suitable configuration, having any suitable size and shape and arranged so that suction tool 38 can be navigated to, and snugly fitted into Eustachian tube 50 to enable suctioning material therefrom and cleaning surface 68 and other parts of Eustachian tube 50. For example, opening 72 may be replaced by one or more openings along the distal end of suction tool 38, this configuration enables removing material from other cavities or anatomical tubes having a different geometry. Note that the flexibility of tubes 54 and 58 provides physician 24 with the capability to navigate and insert suction tool to various organs, such as in brain surgical applications or in small blood vessels in the body of patient 22.

Figure 3:
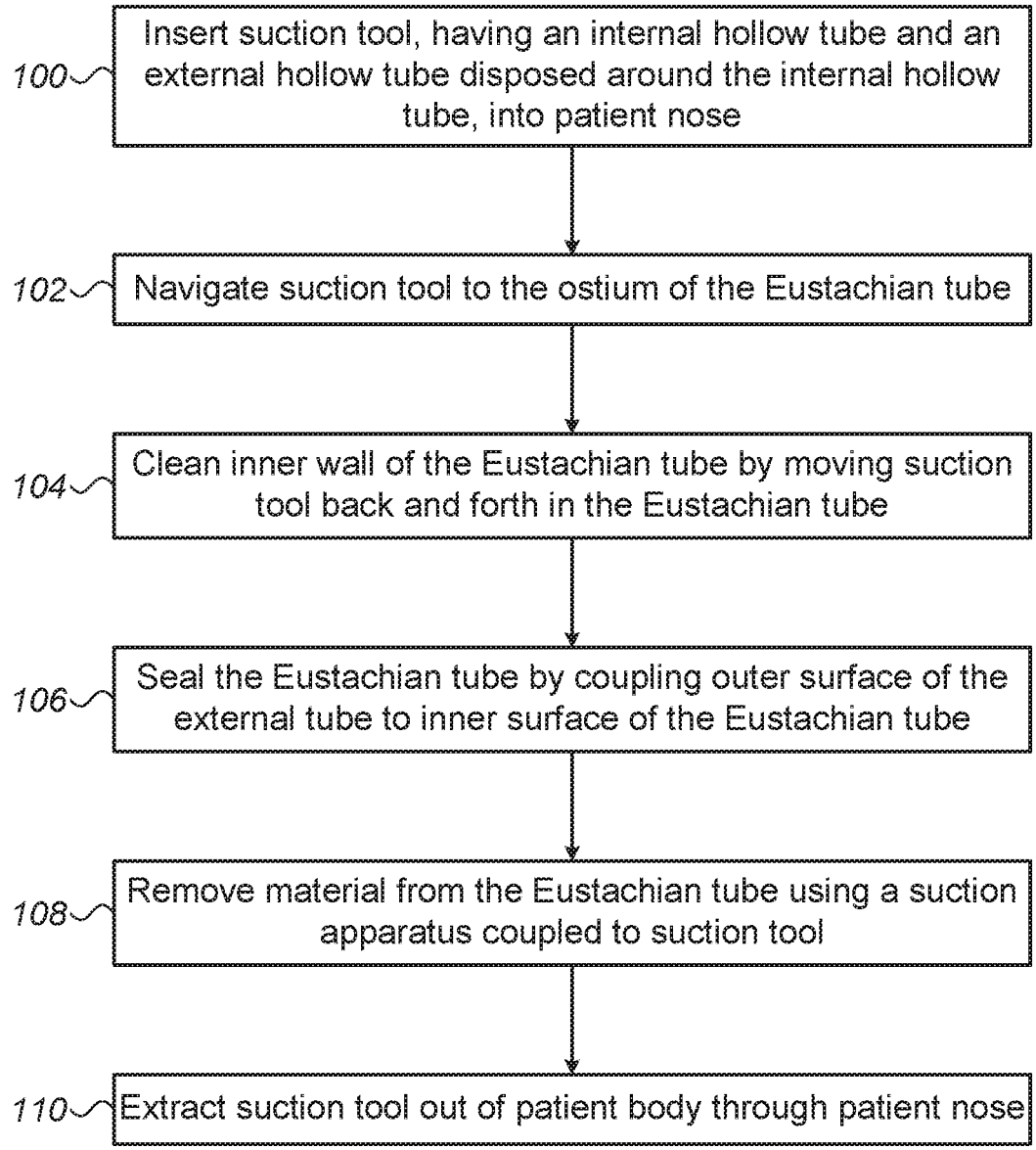
FIG. 3 is a flow chart that schematically illustrates a method for suctioning material from a Eustachian tube, in accordance with an embodiment of the present invention.

FIG. 3 is a flow chart that schematically illustrates a method for suctioning material from Eustachian tube 50, in accordance with an embodiment of the present invention. The method begins with an insertion step 100, in which physician 24 insert suction tool 38, which comprises internal hollow tube 54 and external hollow tube 58 disposed around tube 54, into patient nose 26.

At a navigation step 102, physician 24 navigates suction tool 38 to ostium 66 of Eustachian tube 50, using the tracked position of sensor 64 displayed in image 35. At a cleaning step 104, which is an optional step in this method, physician 24 cleans inner walls 68 of Eustachian tube 50 by moving suction tool 38 back and forth in along walls 68, thereby peeling undesired material off walls 68 of Eustachian tube 50.

At a sealing step 106, physician 24 seals Eustachian tube 50 by coupling outer surface 70 of external tube 58 to inner surface 68 of Eustachian tube 50. At a suctioning step 108, physician 24 removes undesired material, such as dirt, mucus, and infectious fluid, from Eustachian tube 50, using suction apparatus 30, which is coupled to the proximal end of suction tool 38. At an extraction step 110, which concludes this method, physician 24 extracts suction tool 38 out of the body of patient 22, through patient nose 26.

In alternative embodiments, physician 24 may change the order of at least some of the steps of the method. For example, physician 24 may carry out cleaning step 104 after suctioning step 108, and then repeat sealing step 106 and suctioning step 108 so as to clean the material peeled off walls 68 at cleaning step 104.

Although the embodiments described herein mainly address removing material from the Eustachian tube, the methods and systems described herein can also be used in other applications, such as in suctioning undesired material from any other cavity of the ENT system or any other anatomical system of the body.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

What is claimed is:

1. A method, comprising:
   (a) inserting into a patient body a medical suction tool, which comprises a hollow first tube for removing material away from a Eustachian tube of a patient, and a hollow second tube disposed around the first tube;
   (b) navigating the medical suction tool to the Eustachian tube;
   (c) cleaning the Eustachian tube by moving the medical suction tool along sidewalls of the Eustachian tube;
   (d) sealing the Eustachian tube by coupling an outer surface of the second tube to an inner surface of the Eustachian tube; and
   (e) while the Eustachian tube is sealed by the second tube, removing the material away from the Eustachian tube via the first tube,
   wherein cleaning the Eustachian tube comprises moving the medical suction tool back-and-forth along the sidewalls of the Eustachian tube, wherein moving the medical suction tool back-and-forth comprises:
      (i) moving the medical suction tool from a first ostium toward a second ostium,
      (ii) arresting movement of the medical suction tool prior to reaching the second ostium, and
      (iii) moving the medical suction tool toward the first ostium.

2. The method according to claim 1, wherein at least one of the first and second tubes is flexible.

3. The method according to claim 1, wherein navigating the medical suction tool comprises tracking a position of the medical suction tool using a position sensor of a position tracking system, which is coupled to a distal end of the medical suction tool and produces position signals that are indicative of the position of the position sensor.

4. The method according to claim 3, wherein tracking the position comprises tracking a magnetic position sensor comprising a single coil.

5. The method according to claim 1, wherein inserting the medical suction tool comprises inserting the medical suction tool through a nose of the patient.

6. The method according to claim 1, wherein removing the material comprises drawing the material away from the Eustachian tube by applying suction using a suction apparatus coupled to the medical suction tool.

7. The method according to claim 1, further comprising:
   (a) measuring an inner surface of the Eustachian tube; and
   (b) selecting a suction tube having an external diameter that can fit into the Eustachian tube.

8. The method according to claim 1, wherein cleaning the Eustachian tube comprises peeling the material off the sidewalls of the Eustachian tube.

9. The method according to claim 1, wherein the second tube has an outer diameter similar to an inner diameter of the Eustachian tube.

10. The method according to claim 5, wherein navigating the medical suction tool comprises navigating the medical suction tool from the nose of the patient to the Eustachian tube through the first ostium of the patient, wherein the first ostium is positioned between the nose and the Eustachian tube.

11. The method according to claim 5, further comprising extracting the medical suction tool from the patient body through the nose of the patient.

12. A method, comprising:
   (a) inserting a medical suction tool into a body of a patient, wherein the medical suction tool comprises at least one tube;
   (b) navigating the medical suction tool to a Eustachian tube of the patient via at least one anatomical passageway of the patient;
   (c) sealingly engaging an outer surface of the at least one tube with an inner surface of the Eustachian tube;
   (d) while the outer surface of the at least one tube is sealingly engaged with the inner surface of the Eustachian tube, suctioning material away from the Eustachian tube via the at least one tube; and
   (e) cleaning the Eustachian tube by moving the medical suction tool back-and-forth along sidewalls of the Eustachian tube, wherein moving the medical suction tool back-and-forth comprises:
      (i) moving the medical suction tool from the first ostium toward a second ostium,
      (ii) arresting movement of the medical suction tool prior to reaching the second ostium, and
      (iii) moving the medical suction tool toward the first ostium.

13. The method according to claim 12, further comprising peeling the material off the inner surface of the Eustachian tube via the at least one tube.

14. The method according to claim 13, wherein peeling the material includes moving the at least one tube along the inner surface of the Eustachian tube.

15. The method according to claim 12, wherein the at least one tube includes an inner tube and an outer tube, wherein sealingly engaging includes sealingly engaging an outer surface of the outer tube with the inner surface of the Eustachian tube.

16. The method according to claim 15, wherein suctioning the material includes suctioning the material away from the Eustachian tube via the inner tube.

17. A method, comprising:
   (a) inserting a medical suction tool into a body of a patient, wherein the medical suction tool comprises at least one tube;
   (b) navigating the medical suction tool to a Eustachian tube of the patient via at least one anatomical passageway of the patient;
   (c) sealingly engaging an outer surface of the at least one tube with an inner surface of the Eustachian tube;
   (d) while the outer surface of the at least one tube is sealingly engaged with the inner surface of the Eustachian tube, suctioning material away from the Eustachian tube via the at least one tube; and
   (e) cleaning the Eustachian tube by moving the medical suction tool back-and-forth along sidewalls of the Eustachian tube, wherein moving the medical suction tool back-and-forth comprises:
      (i) moving the medical suction tool from the first ostium toward a second ostium,
      (ii) arresting movement of the medical suction tool prior to reaching the second ostium, and
      (iii) moving the medical suction tool toward the first ostium.

18. The method according to claim 17, wherein sealing the Eustachian tube includes coupling an outer surface of the at least one tube to an inner surface of the Eustachian tube.

* * * * *